(12) United States Patent
Gabele

(10) Patent No.: US 6,889,832 B2
(45) Date of Patent: May 10, 2005

(54) STERILE CONTAINER

(75) Inventor: Lorenz Gabele, Sauldorf (DE)

(73) Assignee: AESCULAP AG & Co. KG, Tuttlingen (DE)

( * ) Notice: Subject to any disclaimer, the term of this patent is extended or adjusted under 35 U.S.C. 154(b) by 13 days.

(21) Appl. No.: 10/057,736

(22) Filed: Jan. 25, 2002

(65) Prior Publication Data

US 2002/0098138 A1 Jul. 25, 2002

Related U.S. Application Data

(63) Continuation of application No. PCT/EP00/06124, filed on Jun. 30, 2000.

(30) Foreign Application Priority Data

Jul. 30, 1999 (DE) .......................................... 199 35 986

(51) Int. Cl.⁷ ............................................... B65D 83/10
(52) U.S. Cl. ....................... 206/370; 206/538; 206/571; 206/213.1; 422/300
(58) Field of Search ................................ 206/370, 366, 206/363, 534.1, 539, 438, 439, 538, 571, 213.1; 422/300, 292

(56) References Cited

U.S. PATENT DOCUMENTS

| | | | | |
|---|---|---|---|---|
| 3,703,955 A | * | 11/1972 | Inacker .......................... 206/532 |
| 4,106,620 A | * | 8/1978 | Brimmer et al. ............. 206/363 |
| 4,163,496 A | * | 8/1979 | Dogliotti ...................... 206/538 |
| 4,190,153 A | * | 2/1980 | Olsen ........................... 206/362 |
| 4,344,532 A | * | 8/1982 | Eldridge et al. ............. 206/370 |
| 4,402,407 A | * | 9/1983 | Maly ............................ 206/438 |
| 4,444,310 A | | 4/1984 | Odell |
| 4,793,492 A | * | 12/1988 | Halbich ........................ 206/538 |
| 4,909,382 A | * | 3/1990 | Cuppari ....................... 206/5.1 |
| 4,989,733 A | * | 2/1991 | Patry ............................ 206/570 |
| 5,004,106 A | * | 4/1991 | Blumstock et al. ......... 206/581 |
| 5,172,810 A | * | 12/1992 | Brewer ........................ 206/369 |
| 5,324,489 A | | 6/1994 | Nichols et al. |
| 5,379,899 A | * | 1/1995 | Thurell ........................ 206/538 |
| 5,509,573 A | | 4/1996 | Campoli |
| 5,732,821 A | | 3/1998 | Stone et al. |
| 6,051,186 A | * | 4/2000 | Bond et al. ..................... 422/22 |
| 6,077,485 A | * | 6/2000 | Baker ........................... 422/300 |
| 6,217,835 B1 | * | 4/2001 | Riley et al. .................. 422/297 |

FOREIGN PATENT DOCUMENTS

| | | |
|---|---|---|
| DE | 29 52 733 | 7/1981 |
| EP | 0 513 614 | 11/1992 |
| WO | WO 92/00705 | 1/1992 |
| WO | WO 95/09579 | 4/1995 |

* cited by examiner

*Primary Examiner*—Jila M. Mohandesi
(74) *Attorney, Agent, or Firm*—Barry R. Lipsitz; Douglas M. McAllister

(57) ABSTRACT

In order to design a sterile container for the accommodation and sterile storage, in particular, of surgical instruments or material, comprising a receiving area formed by a container base and container walls, such that it is easy and inexpensive to use it is suggested that the receiving area comprise a plurality of separate chambers and that each chamber have its own closure element.

18 Claims, 2 Drawing Sheets

STERILE CONTAINER

This application is a continuation of international application number PCT/EP00/06124 fied on Jun. 30, 2000.

The present disclosure relates to the subject matter disclosed in International application No. PCT/EP00/06124 of Jun. 30, 2000, which is incorporated herein by reference in its entirety and for all purposes.

BACKGROUND OF THE INVENTION

The invention relates to a sterile container for the accommodation and sterile storage, in particular, of surgical instruments or material, comprising a receiving area formed by a container base and container walls.

Medical instruments and, in particular, surgical instruments for ward or outpatient requirements have to be stored in a sterile manner until they are used. For this purpose, soft packs are mainly used, i.e. the instruments or the material are sealed in sterilization packs. The packaging of instruments and material and the sealing of the packs can take considerable time.

Known sterile containers have a relatively high price in comparison with soft packs.

The object of the invention is to design a generic sterile container such that it is easy and inexpensive to use.

SUMMARY OF THE INVENTION

This object is accomplished in accordance with the invention, for a sterile container of the type described at the outset, in that the receiving area comprises a plurality of separate chambers and that each chamber has its own closure element.

As a result of providing a plurality—i.e. at least two—separate chambers, the inventive sterile container may be filled with a corresponding plurality of instruments and surgical material, respectively, and sterilized at the same time. As a result, it is possible to save time in comparison with the packaging of the instruments and the sealing of the packs. If the articles which are to be stored in the chambers in a sterile manner are designed such that they may be sterilized automatically, an entire sterile container may be sterilized with the instruments accommodated therein in an automatic device and so a "series sterilization" can be achieved which may, again, mean a saving on time and costs.

Prior to using the instruments and material, respectively, stored in a sterile manner, a user opens only the closure element of that chamber, in which the instrument or material required by him is contained. The other chambers remain unopened and thus sterile. In the case of the sterile containers known thus far from the state of the art, it was a disadvantage that the entire sterile container had to be opened in order to remove one instrument and, therefore, all the other instruments became non-sterile insofar as they were not used immediately.

In the case of operations, for which a defined type and/or number of instruments are required, for example, in the case of ear, nose and throat operations, an inventive sterile container which is designed accordingly may be equipped with the required set of instruments and these are kept sterile ready for the operation in a well-organized manner.

In addition, in contrast to bag packs, an inventive sterile container may be used again following cleaning and disinfection.

In a particularly favorable embodiment from a constructional point of view, a chamber has a cover as closure element. This also makes it possible to carry out the cleaning process and disinfection process for the sterile container—possibly with instruments already inserted—more or less automatically.

In a variation of one embodiment it is provided for the closure element to be arranged so as to be pivotable. As a result, closing (for the sterile storage of an instrument or of surgical material in the chamber) or opening (for removal) may be brought about in a simple manner. It may also be provided for a closure element to be arranged by means of a sliding guide means.

It is particularly advantageous when the closure element is at least partially transparent. In this way an operator can easily recognize what is stored in a chamber. It may also be provided for the sterile container to be manufactured at least partially from a transparent material.

In order to obtain a sterile closure in relation to the surroundings, a seal is favorably seated between the chamber and the (closed) closure element. It is particularly favorable when the seal can be acted upon by underpressure. As a result, it is possible for the closure element or a receiving element of a chamber for the seal (depending on which element holds the seal) to be secured by suction to the seal during closing in order to achieve a particularly good seal in relation to the surroundings.

It may be provided for the sterile container to have openings in the container base and/or outer container walls. As a result, the cleaning/disinfection is facilitated, on the one hand, since cleaning/disinfection fluids can flow away through the openings. On the other hand, the possibility is also created, as a result, of condensation water or steam being able to exit from a closed chamber.

A sterile filter is then provided for covering the openings; this sterile filter can, in particular, be a permanent sterile filter. Such a sterile filter prevents non-sterile air from passing into the chambers. On the other hand, water or steam, which can represent a nutrient medium for germs when collected in a chamber, can, nevertheless, still be discharged from the chamber to the surroundings via the sterile filter.

It is particularly advantageous when a sterile filter and, in particular, a single sterile filter is provided for several chambers. As a result, the time required and also the constructional resources for the arrangement of the sterile filter on the sterile container are simplified and, in addition, the sterile filter may be replaced more quickly than several of such filters.

Favorably, the sterile filter is seated beneath the container base. As a result, the container base may be provided with the corresponding openings for the discharge of steam/water or for the discharge of fluids during the cleaning and disinfection and such a cleaning and disinfection process can also be carried out with instruments inserted, wherein a good discharge of the fluids is achieved and the instruments need not be held in addition.

Favorably, the inventive sterile container has a holder for a sterile filter in order to be able to replace sterile filters in this way or to be able to arrange the sterile filter on the inventive sterile container after a cleaning and disinfection process.

In a variation of one embodiment, it may be provided for the holder to be detachable from the sterile container. As a result, the cleaning and disinfection process may be made easier in certain circumstances. It may, however, also be provided for the holder to be arranged so as to be pivotable in order to pivot it away, in particular, from the container base in this way during a cleaning and disinfection process.

It is particularly advantageous when the sterile filter is held in the holder by means of a spring catch. The sterile filter may then be replaced in a simple and quick way and, on the other hand, it is held securely in the holder in order to prevent non-sterile air from passing into a closed chamber.

Favorably, it is provided for a protective grating to be seated between sterile filter and container. This protective grating has the task of avoiding any penetration of the sterile filter by, in particular, pointed instruments which are stored in the sterile container, i.e. to protect the sterile filter from leakage. When the protective grating is permeable to steam, water vapor or water from the interior of a closed chamber can be discharged.

The protective grating can be favorably inserted into a holder for the sterile filter. As a result, only one holder for the sterile filter and the protective grating need be provided.

Favorably, a chamber has a respective limiting element provided with openings facing the sterile filter. These openings facilitate the cleaning and disinfection of the chamber and water or water vapor can also be discharged from the chamber through them when an instrument or surgical material is stored in it. It is particularly simple from a constructional point of view when the limiting element is a respective part of the container base.

Favorably, a limiting element provided with openings for several chambers is formed in one piece. In this respect, gaps between adjacent limiting elements, in which germs can collect, are, for example, avoided.

In a variation of one embodiment, it is favorably provided for the limiting element provided with openings of one chamber to be detachable. As a result, the assembly of the inventive sterile container is, on the one hand, made easier. On the other hand, the limiting element provided with the openings can be cleaned more easily when an inventive sterile container is utilized again or thrown away and a new limiting element inserted. If the openings are, in particular, very narrow, germs can collect in them and it may be more advantageous to use a new limiting element instead of a time-consuming cleaning and disinfection.

The following description of preferred embodiments of the invention serves to explain the invention in greater detail in conjunction with the drawings.

Figure 1:
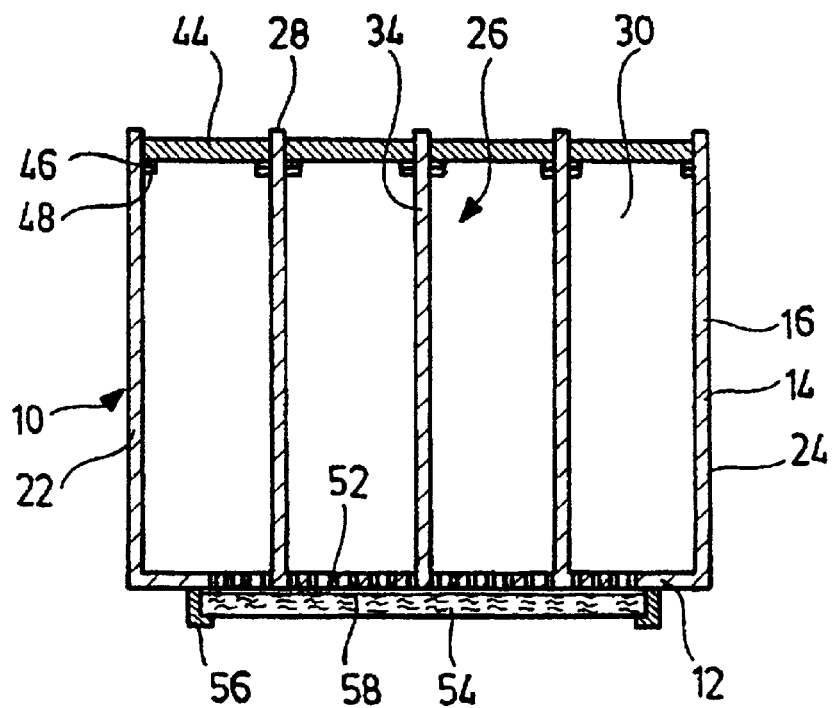
FIG. 1 shows a lateral sectional illustration of a sterile container.

A sterile container which is designated as a whole as 10 in FIG. 1 comprises a container base 12 and container walls 14. The container walls themselves comprise outer walls 16, i.e. a front wall 18, a rear wall 20, a left-hand side wall 22 and a right-hand side wall 24 (FIG. 2).

A receiving area 26 is formed within these outer walls 18, 20, 22, 24, limited by the container base 12. This area is, on the other hand, subdivided into a plurality of separate chambers 30 by intermediate walls 28 which extend between the outer walls 16.

Figure 2:
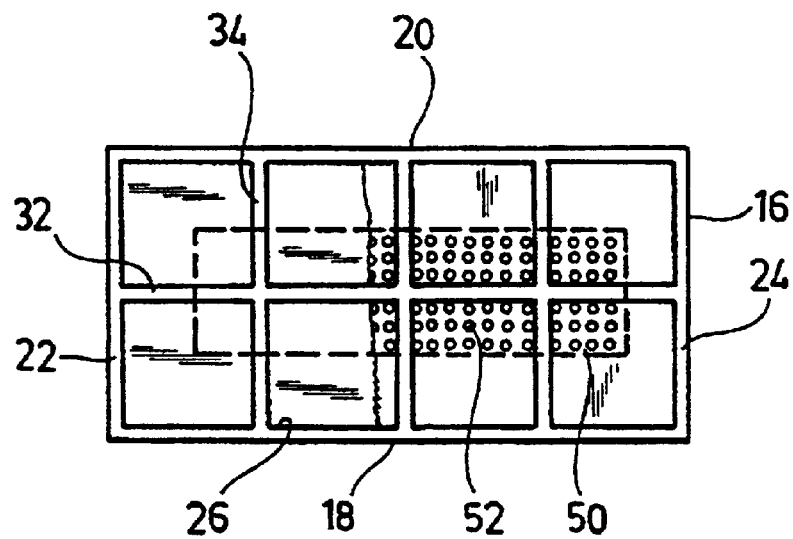
FIG. 2 shows a plan view of the sterile container of FIG. 1.

In the case of the embodiment shown in FIGS. 1 and 2, the receiving area 26 is subdivided into eight chambers 30 which have the same cross section and the same height. For this purpose, a longitudinal intermediate wall 32 runs centrally between the left-hand side wall 22 and the right-hand side wall 24 and three transverse intermediate walls 34 extend between the front wall 18 and the rear wall 20 at equal distances. The intermediate walls 32, 34 are designed such that the individual chambers 30 are closed so as to be fluid-tight and gas-tight in relation to one another.

Figure 3:
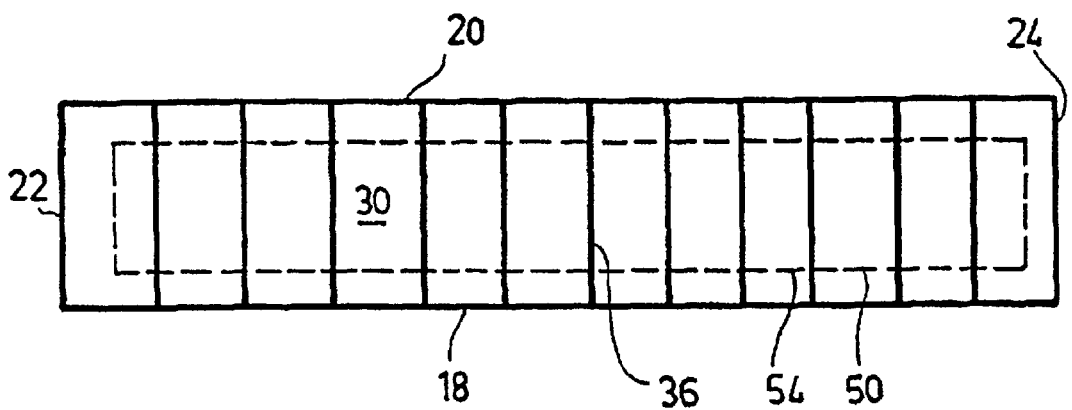
FIG. 3 shows a plan view of a second embodiment of a sterile container.

In the case of the additional embodiment shown in FIG. 3, a single-line chamber subdivision in comparison with the first embodiment according to FIGS. 1, 2 is shown, with which no longitudinal intermediate wall 32, as in FIG. 2, is provided. A fine chamber subdivision is achieved in this embodiment as a result of the provision of a plurality of parallel transverse intermediate walls 36.

Figure 4:
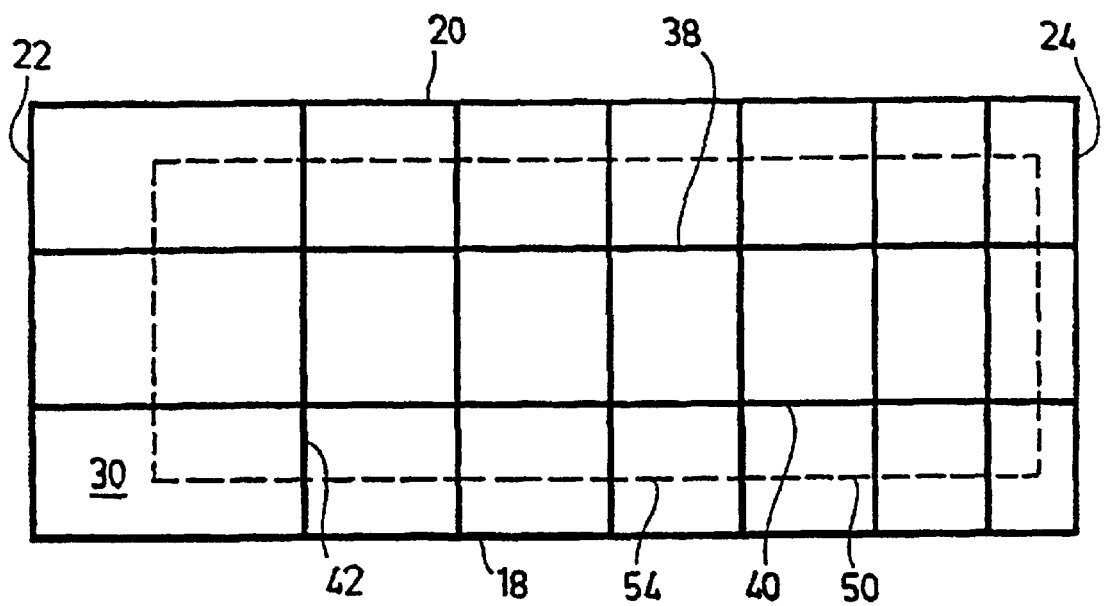
FIG. 4 shows a further embodiment of an inventive sterile container.

In the case of the embodiment shown in FIG. 4, a first longitudinal intermediate wall 38 and a second longitudinal intermediate wall 40 at a distance thereto are arranged parallel to the front wall 18 and the rear wall 20, respectively, so that a chamber subdivision with three lines is brought about.

Transverse intermediate walls 42 are arranged at a distance from one another parallel to the left-hand side wall 22 and the right-hand side wall 24, respectively. This distance need not, however, be uniform and so individual chambers 30 can have a different cross section. As a result, an asymmetric chamber subdivision can be achieved.

It is a matter of course that a plurality of variation possibilities with respect to the subdivision of the container result due to the selection of the outer dimensions of the inventive sterile container, i.e. due to corresponding dimensioning of the container base 12 and the outer walls 16 as well as corresponding arrangement and dimensioning of the intermediate walls 28.

Each chamber 30 has, as shown in FIG. 1, its own closure element 44, which is, in particular, a cover or lid. As a result, the chamber 30 is closed so as to be germ-tight relative to the outside (sealed against the penetration of germs) with a closed closure element 44 such that the sterilized articles, such as a set of surgical instruments or other surgical material, received by a cleaned and likewise sterilized chamber remain sterile in the chamber 30.

An individual closure element 44 for the associated chamber 30 is arranged, for example, so as to be pivotable on it (not shown in the drawings) so that the chamber 30 can be opened by pivoting the associated closure element 44 and the, for example, surgical material stored in a sterile manner in the chamber 30 can be accessed in this way. In an alternative embodiment, it may also be provided for a closure element 44 to be opened and closed by means of a sliding guide means. Such a sliding guide means may be used, in particular, in a single-line embodiment of the sterile container, as shown in FIG. 3.

A seal 46 is advantageously arranged between a closure element 44 in its closed state and the chamber 30. For example, the corresponding container walls (side walls 22, 24, transverse intermediate walls 34, longitudinal intermediate walls 32) have, for this purpose, corresponding projections 48 which serve as support for the associated closure element 44 (in the case of a pivotable arrangement). The seal 46 is then seated on these projections 48 facing the closure element 44 so that, with a closed closure element 44, this causes a sealing of the chamber 30 in relation to the surroundings. The seal 46 may be a seal acted upon by underpressure which is securely seated, in particular, on the projections 48 (for example, by means of an adhesive connection) and when the closure element 44 is closed is secured on this by way of suction in order to bring about an increased leak-tightness.

The container base has an opening element 50 which is provided with openings 52 which preferably extend parallel to the container walls 14 and at right angles to the container base 12 through it. The opening element 50 is dimensioned such that each chamber 30 of the sterile container 10 has such openings 52 in its base.

It may, in particular, be provided for the opening element 50 to not be formed in one piece with the rest of the sterile container 10 but rather to be removable.

A sterile filter 54 is seated between the outside and the openings 52 and this prevents non-sterile air from passing into the chambers 30 via the openings 52 and thus making articles stored in the chambers 30 non-sterile. However, the sterile filter 54 facilitates, on the other hand, a passage of water vapor from the chambers 30 to the surroundings. The sterile filter 54 is, in particular, a permanent sterile filter, such as, for example, a filter consisting of PTFE (polytetrafluoroethylene) or a ceramic filter. The sterile filter 54 has somewhat larger dimensions than the opening element 50 in order to prevent non-sterile air from being able to pass into the sterile container 10 (FIG. 1).

The inventive sterile container 10 has a holder 56 for the sterile filter 54. This is designed, for example, such that it has a spring catch, by means of which the sterile filter 54 may be inserted into it and snaps shut when a predetermined position is reached (in which all the openings 52 can be covered) in order to make a quick insertion or change of the sterile filter 54 possible, on the one hand, and, on the other hand, to bring about a secure covering of the openings 52.

The holder 56 is advantageously arranged on the sterile container 10 so as to be pivotable so that it can be pivoted away, in particular, during a cleaning process of the sterile container 10.

In addition, it may be provided for a protective grating 58 to be seated in the holder 56 between the sterile filter 54 and the openings 52. This protective grating 58, which consists, for example, of metal, is of such a close-meshed design that it protects the sterile filter 54 from any penetration by a pointed instrument possibly stored in a chamber 30. In this respect, it may be provided, in particular, for the width of the mesh and a width of the webs of a mesh-forming netting to be selected such that as few residues as possible from the washing and disinfection process remain on the protective grating 58. In order to make an exchange of steam with the surroundings possible, the protective grating 58 must be permeable to steam.

The closure elements 44 are preferably designed to be at least partially transparent so that an operator can recognize sets of surgical instruments or material stored in a chamber 30 even when a closure element 44 is closed. It may also be provided for one or several container walls 14 to be of a transparent design in order to facilitate the view from outside of the articles stored in the chambers 30.

The inventive sterile container may be used as follows:

When closure elements 44 are opened or removed and when a sterile filter 54 is not inserted or a holder 56 is pivoted away, instruments to be sterilized are placed in the respective chambers 30 or are already in the chambers, into which they have been returned after use. The (open) sterile container 10 with the "filled" chamber 30 is then prepared, i.e. a cleaning and disinfection process is carried out. The cleaning and disinfection fluid may flow away via the openings 52. Subsequently, the closure elements 44 are closed and the sterile filter 54 inserted in order to then sterilize the entire container.

Prior to using the respective instrument or surgical material, an operator opens via the associated closure element 44 only that particular chamber 30 which contains the desired instrument. The operator can recognize this via the transparent closure element 44. The chambers not opened remain sterile, i.e. the articles stored in them do not become non-sterile due to the opening of another chamber 30.

Cleaning and sterilization methods other than the automatic method described above may also, of course, be used in order to store, in particular, water-sensitive surgical materials, such as bandaging materials, in the chambers 30 in a sterile manner.

What is claimed is:

1. Sterile container for the accommodation and sterile storage of surgical instruments or material, comprising a receiving area formed by a container base and container walls, the receiving area comprising a plurality of separate chambers formed by intermediate walls of the container which divide the receiving area, wherein:

filter openings are provided in said separate chambers;

a singel sterile flter covers the filter openings for several of the chambers;

each chamber has its own separate cover as a closure element, and a seal is seated between each chamber and its closure element and completely seals each the chamber.

2. Sterile container as defined in claim 1, wherein the closure element is arranged so as to be pivotable.

3. Sterile container as defined in claim 1, wherein a closure element is arranged by means of a sliding guide means.

4. Sterile container as defined in claim 1, wherein the closure element is at least partially transparent.

5. Sterile container as defined in claim 1, wherein the sterile container is manufactured at least partially from a transparent material.

6. Sterile container as defined in claim 1, wherein the seal is adapted to be acted upon by underpressure.

7. Sterile container as defined in claim 1, wherein the sterile filter is seated beneath the container base.

8. Sterile container as defined in claim 1, wherein the sterile container has a holder for the sterile filter.

9. Sterile container as defined in claim 8, wherein the holder is detachable from the sterile container.

10. Sterile container as defined in claim 8, wherein the holder is arranged on the sterile container so as to be pivotable.

11. Sterile container as defined in claim 8, wherein the sterile filter is held in the holder by means of a spring catch.

12. Sterile container as defined in claim 1, wherein a protective grating is seated between sterile filter and sterile container.

13. Sterile container as defined in claim 12, wherein the protective grating is permeable to steam.

14. Sterile container as defined in claim 12, wherein the protective grating is insertable into a holder for the sterile filter.

15. Sterile container as defined in claim 1, wherein at least one chamber has a limiting element provided with openings facing the sterile filter.

16. Sterile container as defined in claim 15, wherein the limiting element is a respective part of the container base.

17. Sterile container as defined in claim 16, wherein a limiting element provided with openings for several chambers is formed in one piece.

18. Sterile container as defined in claim 15, wherein the limiting element provided with openings of the at least one chamber is detachable.

* * * * *

UNITED STATES PATENT AND TRADEMARK OFFICE
CERTIFICATE OF CORRECTION

PATENT NO.     : 6,889,832 B2
DATED          : May 10, 2005
INVENTOR(S)    : Lorenz Gabele It is certified that error appears in the above-identified patent and that said Letters Patent is hereby corrected as shown below:

Column 6,
Line 8, "singel" should read -- single --; and "flter" should read -- filter --.
Line 13, "and completely seals each the chamber" should read -- to completely seal the chamber --.

Signed and Sealed this

Twenty-third Day of August, 2005

JON W. DUDAS
*Director of the United States Patent and Trademark Office*